United States Patent [19]

Nisato et al.

[11] Patent Number: 4,822,895
[45] Date of Patent: Apr. 18, 1989

[54] 3-AMINOAZETIDINE, ITS SALTS AND INTERMEDIATES OF SYNTHESIS

[75] Inventors: Dino Nisato, Pavia; Marco Frigerio, Mantova, both of Italy

[73] Assignee: Societe Anonyme - SANOFI, Paris, France

[21] Appl. No.: 703,828

[22] Filed: Feb. 21, 1985

[30] Foreign Application Priority Data

Feb. 27, 1984 [FR] France ................ 84 02951

[51] Int. Cl.$^4$ .......................... C07D 205/04
[52] U.S. Cl. .................................. 548/953; 548/473
[58] Field of Search ............... 260/239 AR; 548/473, 548/953

[56] References Cited

U.S. PATENT DOCUMENTS 3,929,765 12/1975 Suzuki et al. ............. 548/953

FOREIGN PATENT DOCUMENTS 2150816 4/1975 France .
74109369 10/1984 Japan .

OTHER PUBLICATIONS

Gaertner, J. Org. Chem., vol. 35 (11), (1970) p. 3952.
Hasegawa, et al., Chem. Abstracts, vol. 78, (1973), entry 147770v.
Chen, et al., Chem. Abstracts, vol. 77, (1972), entry 34212a.
Cromwell, et al., Chem. Reviews, 79(4), (1979), pp. 331, 344 and 345.
Chen et al., "Azetidines IV. The Reaction of 1-t-Butylazitidinyl-3 Tosylate with Amines and Mercaptans", *Bulletin of the Chemical Society of Japan*, vol. 41, pp. 712–716 (1968).
Chem. Abstracts 83: 9760u Jul. 7, 1975.

*Primary Examiner*—Donald G. Daus
*Assistant Examiner*—C. Cseh
*Attorney, Agent, or Firm*—Foley & Lardner, Schwartz, Jeffery, Schwaab, Mack, Blumenthal & Evans

[57] ABSTRACT

The 3-aminoazetidine, its salts, new intermediates of formula

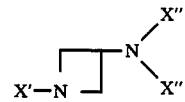

wherein X' represents hydrogen or a protecting group and both X" represent hydrogen or, together with the nitrogen atom, a phthalimido group, X' not and both X" being hydrogen at the same time; a process for the preparation of the 3-aminoazetidine, starting from a 1-protected 3-sulfonyloxyazetidine by reaction with the potassium phthalimide and transformation of the above mentioned intermediates.

13 Claims, No Drawings

3-AMINOAZETIDINE, ITS SALTS AND INTERMEDIATES OF SYNTHESIS

The present invention relates to the 3-aminoazetidine of formula

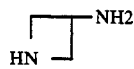

I to its salts, to a process for their preparation and to intermediates useful for the synthesis of the product.

The 3-aminoazetidine has never been described in the literature. Actually, the azetidine ring is particularly sensitive to the hydrolytic conditions which provoke its opening in the presence of water or of a nucleophilic radical (C. Mannich, G. Paumgarter, Chem. Ber. 1937, 70, 210-213). It is also possible that the opening of the ring gives rise to a polymerization reaction (C. F. Gibbs, C. S. Harvel, J. Am. Chem. Soc. 1935, 57, 1137-1139).

Thus, it is possible to prepare, according to known methods, a 3-aminoazetidine which is substituted on the primary amino group by various radicals, but literature does not teach how to prepare an azetidine having a free amino group in the 3-position.

It has now been found that the 3-aminoazetidine can be prepared starting from a 3-sulfonyloxyazetidine having its nitrogen atom protected. By substituting the sulfonyloxy group by a phthalimido group, new intermediates are obtained which, by two subsequent reactions of hydrolysis and catalytic hydrogenation give the 3-aminoazetidine in the form of one of its salts.

Thus, it is an object of the present invention to provide the 3-aminoazetidine of formula I above and its addition salts with inorganic or organic acid such as the hydrochloride, hydrobromide, sulfate, acetate, maleate, fumarate, oxalate, picrate, methanesulfonate and the like.

These products are useful in the preparation of the corresponding 1-substituted compounds having psychotropic action. More particularly, by protecting the cyclic nitrogen atom in the form of benzhydryl, the 3-acetylamino derivative is prepared which, after the elimination of the benzhydryl group and subsequent reaction with 2,6-dichloropyridine, gives a compound which, by acid hydrolysis, yields the 3-amino-1-(6-chloropyrid-2-yl)azetidine having an anorexigenic activity at a dosis of 15 mg/kg per os in the food intake test in rats.

It is another object of the present invention, to provide a process for the preparation of the 3-aminoazetidine and of its salts, which comprises treating a 1-protected 3-sulfonyloxyazetidine of formula

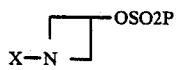

II wherein R represents an alkyl group of from 1 to 4 carbon atoms, a phenyl group or a tolyl group and X represents a protecting group, with an alkali metal phthalimide, submitting the 1-protected 3-phthalimidoazetidine to two subsequent reactions, of hydrolysis with a 60-90% aqueous solution of hydrazine and of catalytic hydrogenation or, when the protecting group is the trityl group, of a hydrolysis under mild acid conditions and converting the product thus obtained into its addition salts with inorganic or organic acids.

The preferred protecting groups include the optionally substituted benzyl, the optionally substituted benzhydryl, the optionally substituted trityl and the 2,2,2-trichloroethyl group. A preferred substituting group of benzyl, benzhydryl and trityl is the methoxy group.

The process of the present invention is represented by the following scheme

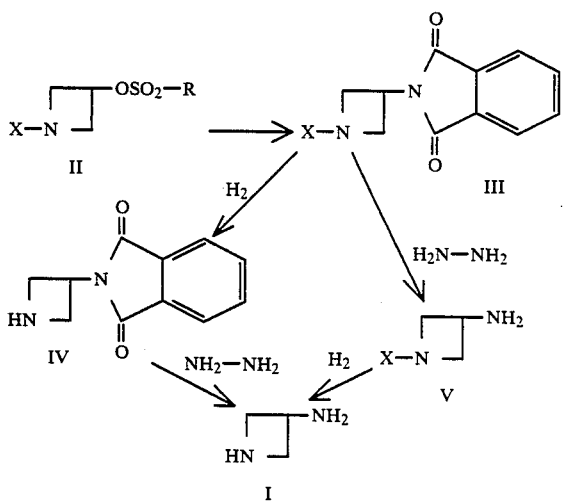

wherein X and R are as hereinabove defined.

The reaction between the 1-substituted 3-sulfonyloxyazetidine (II) and the alkali metal phthalimide, preferably potassium phthalimide, is carried out in an organic solvent, such as toluene, hexane and the like in the presence of a phase transfer catalyst, such as an ammonium or phosphonium salt, i.e. tetrabutylammonium bromide or hexadecyltributylphosphonium bromide at a temperature of from 100° to 140° C.

The 1-substituted 3-phthalimidoazetidine thus obtained may be treated in order to release the protecting group. In general, the deprotection is carried out by catalytic hydrogenation by utilising palladium hydroxide on charcoal in the presence of hydrochloric acid as a suitable catalyst.

The 3-phthalimidoazetidine (IV) thus obtained is hydrolysed with hydrazine. The hydrolysis is carried out in an organic solvent, such as methanol by using hydrazine hydrate.

According to a variant of the process of the present invention, the 1-substituted 3-phthalimidoazetidine of formula III is submitted at first to a hydrolysis reaction with hydrazine under the conditions hereinabove described. Then the 1-substituted 3-aminoazetidine (V) thus obtained is deprotected as hereinabove described for the compound III and the 3-aminoazetidine is isolated in the form of one of its salts.

When the protecting group X present in compounds III and V is the optionally substituted trityl group, the deprotection may be carried out under mild condition of acid hydrolysis, for example by action of a 50% formic acid aqueous solution at a temperature of from 20° to 50° C.

The 3-aminoazetidine can be isolated in the form of a very volatile free base, starting from the corresponding salts and chemically characterized by its transformation into its 1,N-dibenzoyl derivative.

It is a further object of the present invention to provide intermediates useful for the synthesis of the 3-aminoazetidine and of its derivatives on the primary amine, characterized by the following formula

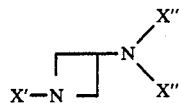

wherein X' represents hydrogen or a protecting group and both X" represent hydrogen or, together with the nitrogen atom, a phthalimido group, X' and both X" being not hydrogen at the same time, and their addition salts with inorganic or organic acids.

The following examples illustrate the invention without limiting it. The NMR spectra have been obtained by means of an apparatus WP-80 CW Brucker at 80 Mhz at a concentration of 5% w/v.

EXAMPLE 1

A mixture of 0.362 mol of 1-benzhydryl-3-mesyloxyazetidine (J. Org. chem. 1972, 37, 3953–3955), 0.44 mol of potassium phthalimide and 0.045 mol of hexadecyltributylphosphonium bromide in 500 ml of anhydrous toluene is heated at reflux for 5 hours, then it is cooled at 20° C. The precipitate is filtered, washed with 400 ml of ethyl acetate and discarded. The organic solution is washed with water, dried on anhydrous sodium sulfate, filtered on charcoal and concentrated under reduced pressure. The oily residue is crystallized from 600 ml of diisopropyl ether. Thus, 80 g (Yield: 67.4% of the theoretic) of 1-benzhydryl-3-phthalimidoazetidine are obtained; m.p. 118°–120° C.

From the mother liquor additional 10 g of product are obtained.

IR: $\nu$max (KBr): 1750, 1710(b), 1390 cm−1.

1H-NMR (CDCl3): $\delta$TMS (ppm): 3.64 (4H, m→d), 4.63 (1H, s), 4.83 (1H, m→t), 7.0–7.8 (14H, m).

Analogously, the same product is obtained with a 20% yield, by using the tetrabutylammonium bromide as a phase transfer catalyst.

EXAMPLE 2

A mixture of 0.244 mol of 1-benzhydryl-3-phthalimidoazetidine in 1000 ml of anhydrous methanol is heated at reflux for 15 minutes, then, after removing the heating bath, 0.339 mol of 85% hydrazine hydrate are added thereto. The mixture is heated at reflux for 30 minutes, then a solid white product begins to precipitate from the limpid solution thus obtained. The mixture is again heated for 90 minutes, then it is cooled at 10° C. One liter of diethyl ether is added to the mixture which is then filtered. After washing with ether, the solid product (35 g) is discarded and the mother-liquor is concentrated under reduced pressure. The residue is taken up with 500 ml of water and the pH of the solution is adjusted to 11 with sodium hydroxide. After extraction with 1 liter of diethyl ether, the ethereal phase is washed with water, dried on anhydrous sodium sulfate and evaporated under reduced pressure. Thus, the 3-amino-1-benzhydrylazetidine is obtained in the form of an oil which tends to solidify Yield 96.3%. By reaction with hydrochloric acid in a ispropanol/acetone mixture, the 3-amino-1-benzhydrylazetidine dihydrochloride is obtained which, after crystallization from isopropanol, melts at 108°–110° C.

1H-NMR (CDCl3): $\delta$TMS (ppm): 1.65 [2H, s(b)], 2.6 (2H, m), 3.5 (3H, m), 4.25 (1H, s), 7.0–7.5 (10H, m) (free base).

EXAMPLE 3

A mixture of 0.044 mol of 3-amino-1-benzhydrylazetidine, 110 ml of anhydrous methanol, 2.8 g of palladium hydroxide on charcoal (Pearlman catalyst, Lot Midy E 21/13-W. M. Pearlman, Tetrahedron Letters 1967, 1663–1664) and 3.6 ml of concentrated hydrochloric acid is hydrogenated at 35°–40° C. for 5 hours under a pressure of 4 bars. Then the reaction mixture is filtered and concentrated under reduced pressure at an external temperature of 40° C. The semi-solid residue is taken up with 110 ml of isopropanol. The 3-aminoazetidine dihydrochloride thus obtained is filtered and dried.

Yield: 4.9 g (76.7%); m.p. 159°–162° C. (dec).

1H-NMR (DMSO-d6)$\delta$TMS (ppm): 4.1 (5H, m), 9.2 [5H, s(b)].

EXAMPLE 4

By operating as described in Example 3, by hydrogenating the 1-benzhydryl-3-phthalimidoazetidine, the 3-phthalimidoazetidine hydrochloride is obtained.

EXAMPLE 5

To a mixture of 20 g of potassium hydroxide and ice, cooled to −5° C., there is added, portionwise, 14 g of 3-aminoazetidine prepared according to Example 3. The oil which separates is decanted off and kept on potassium hydroxide tablets. By distillation under 1 bar argon atmosphere, 1 g of 3-aminoazetidine base is obtained; b.p. 135°–142° C.

The product thus obtained is dissolved in methylene chloride and the resulting solution is treated with two equivalents of benzoyl chloride in methylene chloride. The solution is stirred at room temperature for 8 hours, the residue is taken up with diethyl ether, washed with an aqueous solution of sodium carbonate, dried on anhydrous sodium sulfate and the solvent evaporated. The residue is crystallized from ethyl acetate to obtain the 1-benzoyl-3-benzoyl-aminoazetidine; m.p. 120°–122° C.

Analysis for C17H16N2O2: Calc.: C 72.84, H 5.75, N 9.99. Found: C 72.96, H 5.87, N 9.78.

The IR and NMR spectra confirm the structure of the product.

We claim:

1. A compound selected from the group consisting of 3-aminoazetidine and its addition salts with inorganic or organic acids.

2. 3-Aminoazetidine dihydrochloride.

3. An intermediate of formula

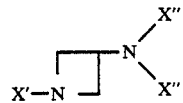

wherein X' represents hydrogen or a protecting group, selected from the group consisting of benzyl, methoxy substituted benzyl, benzhydryl, methoxy substituted benzhydryl, trityl, methoxy substituted trityl and 2,2,2-trichloroethyl, both X" represent hydrogen or, together with the nitrogen atom form a phthalimido group, X' and both X" never being hydrogen at the same time, and its addition salts with organic or inorganic acids.

4. 1-Benzhydryl-3-phthalimidoazetidine and its addition salts with organic or inorganic acids.

5. 3-Amino-1-benzhydrylazetidine and its addition salts with organic or inorganic acids.

6. 3-Amino-1-benzhydrylazetidine hydrochloride.

7. 3-Phthalimidoazetidine and its addition salts with organic or inorganic acids.

8. The compound of claim 1, wherein the addition salt of 3-aminoazetidine with an organic or inorganic acid is selected from the group consisting of the hydrochloride, hydrobromide, sulfate, acetate, maleate, fumarate, oxalate, picrate and methanesulfonate.

9. The compound of claim 4 wherein the addition salt of 1-benzhydryl-3-phthalimidoazetidine with an organic or inorganic acid is selected from the group consisting of hydrochloride, hydrobromide, sulfate, acetate, maleate, fumarate, oxalate, picrate or methanesulfonate.

10. The compound of claim 5, wherein the addition salt of 3-amino-1-benzhydryl-azetidine with an organic or inorganic acid is selected from the group consisting of hydrochloride, hydrobromide, sulfate, acetate, maleate, fumarate, oxalate, picrate or methanesulfonate.

11. The compound of claim 7, wherein the addition salt of 3-phthalimidoazetidine with an organic or inorganic acid is selected from the group consisting of hydrochloride, hydrobromide, sulfate, acetate, maleate, fumarate, oxalate, picrate or methanesulfonate.

12. 1-Benzoyl-3-Benzoyl-amino azetidine.

13. The compound of claim 8, wherein said salt is formed by reaction of one molecule of a 3-aminoazetidine with two molecules of acid.

* * * * *